US012636646B2

(12) United States Patent
Blain Christen et al.

(10) Patent No.: US 12,636,646 B2
(45) Date of Patent: May 26, 2026

(54) SPRING HEATER FOR BIOASSAY

(71) Applicant: ARIZONA BOARD OF REGENTS ON BEHALF OF ARIZONA STATE UNIVERSITY, Scottsdale, AZ (US)

(72) Inventors: Jennifer Mary Blain Christen, Chandler, AZ (US); Clifford L. Anderson, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 760 days.

(21) Appl. No.: 17/971,178

(22) Filed: Oct. 21, 2022

(65) Prior Publication Data
US 2023/0130154 A1 Apr. 27, 2023

Related U.S. Application Data

(60) Provisional application No. 63/270,516, filed on Oct. 21, 2021.

(51) Int. Cl.
| | |
|---|---|
| *B01L 3/00* | (2006.01) |
| *B01L 7/00* | (2006.01) |
| *C12Q 1/6844* | (2018.01) |

(52) U.S. Cl.
CPC ...... *B01L 3/502715* (2013.01); *C12Q 1/6844* (2013.01); *B01L 2300/0654* (2013.01); *B01L 2300/0816* (2013.01); *B01L 2300/1805* (2013.01)

(58) Field of Classification Search
None
See application file for complete search history.

(56) References Cited

U.S. PATENT DOCUMENTS

| | | | | | |
|---|---|---|---|---|---|
| 3,657,517 | A | * | 4/1972 | Hoyt | A61M 16/16 |
| | | | | | 219/442 |
| 6,231,176 | B1 | * | 5/2001 | Peter | B41J 11/0024 |
| | | | | | 347/101 |
| 6,558,947 | B1 | * | 5/2003 | Lund | B01L 7/54 |
| | | | | | 435/303.1 |
| 2004/0235148 | A1 | * | 11/2004 | Shibazaki | B01L 3/50255 |
| | | | | | 435/297.5 |
| 2022/0395332 | A1 | | 12/2022 | Marvi et al. | |

FOREIGN PATENT DOCUMENTS

WO         2021108690 A1         6/2021

OTHER PUBLICATIONS

Webpage titled "Flexible Heaters", <https://web.archive.org/web/20200814072941/https://sea.omega.com/th/prodinfo/flexibleheaters.html>, cached by Internet Archive Aug. 14, 2020 (Year: 2020).*

(Continued)

*Primary Examiner* — Holly Kipouros
(74) *Attorney, Agent, or Firm* — Quarles & Brady LLP

(57) ABSTRACT

An apparatus comprising a flexible heater in thermal contact with a flexible spring, wherein the flexible spring is configured to provide thermal energy from the heater to a cartridge when the cartridge is in contact with the flexible spring. Methods of making and using the same are also disclosed.

9 Claims, 11 Drawing Sheets

(56)             References Cited

OTHER PUBLICATIONS

O. Al-Ahmad, M. Ourak, J. Van Roosbroeck, J. Vlekken and E. V. Poorten, "Improved FBG-Based Shape Sensing Methods for Vascular Catheterization Treatment," in IEEE Robotics and Automation Letters, vol. 5, No. 3, pp. 4687-4694, Jul. 2020, doi: 10.1109/LRA.2020.3003291.

Anderson, Clifford, "Spring Heater for Bioassay—Figures," Aug. 31, 2021.

F. Khan, A. Denasi, D. Barrera, J. Madrigal, S. Sales and S. Misra, "Multi-Core Optical Fibers With Bragg Gratings as Shape Sensor for Flexible Medical Instruments," in IEEE Sensors Journal, vol. 19, No. 14, pp. 5878-5884, 15 Jul. 15, 2019, doi: 10.1109/JSEN.2019.2905010.

Mandal, K., Parent, F., Martel, S. et al. Vessel-based registration of an optical shape sensing catheter for MR navigation. Int J CARS 11, 1025-1034 (2016). https://doi-org.ezproxy1.lib.asu.edu/10.1007/s11548-016-1366-7.

Miralles, V., Huerre, A., Malloggi, F., & Jullien, M.-C. (2013). A Review of Heating and Temperature Control in Microfluidic Systems: Techniques and Applications. Diagnostics, 3(1), 33-67. https://doi.org/10.3390/diagnostics3010033.

R. J. Roesthuis and S. Misra, "Steering of Multisegment Continuum Manipulators Using Rigid-Link Modeling and FBG-Based Shape Sensing," in IEEE Transactions on Robotics, vol. 32, No. 2, pp. 372-382, Apr. 2016, doi: 10.1109/TRO.2016.2527047.

C. Shi et al., "Shape Sensing Techniques for Continuum Robots in Minimally Invasive Surgery: A Survey," in IEEE Transactions on Biomedical Engineering, vol. 64, No. 8, pp. 1665-1678, Aug. 2017, doi: 10.1109/TBME.2016.2622361.

* cited by examiner

100

200

200

202

201

SPRING HEATER FOR BIOASSAY

CROSS-REFERENCE TO RELATED APPLICATIONS

This application is related to, claims priority to, and incorporates herein by reference for all purposes U.S. Provisional Patent Application No. 63/270,516, filed Oct. 21, 2021.

BACKGROUND OF THE INVENTION

There is a need in the art for a low-cost and easy-to-use method to process a biofluid and perform nucleic acid amplification testing in a point of care device that reduces the likelihood of exposing a user to reagents, and protects the reagents from exposure to excessive temperature.

BRIEF SUMMARY OF THE INVENTION

The present disclosure provides an apparatus comprising a flexible heater in thermal contact with a flexible spring. The flexible spring is configured to provide thermal energy from the heater to a microfluidic cartridge received by the apparatus when the microfluidic cartridge is in contact with the flexible spring.

In another aspect, the disclosure provides an apparatus comprising a case encasing a heater and a flexible spring, where the case is dimensioned to receive a microfluidic cartridge. The flexible spring positions the received microfluidic cartridge in thermal communication with the heater when the received microfluidic cartridge is in contact with the flexible spring.

In another aspect, the present disclosure provides a method of heating a microfluidic cartridge in contact with the flexible spring of the apparatus, where the microfluidic cartridge has a biofluid sample. Heating the microfluidic cartridge with the apparatus provides sufficient thermal energy to perform an amplification reaction to generate amplification products of a target nucleic acid.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1A:
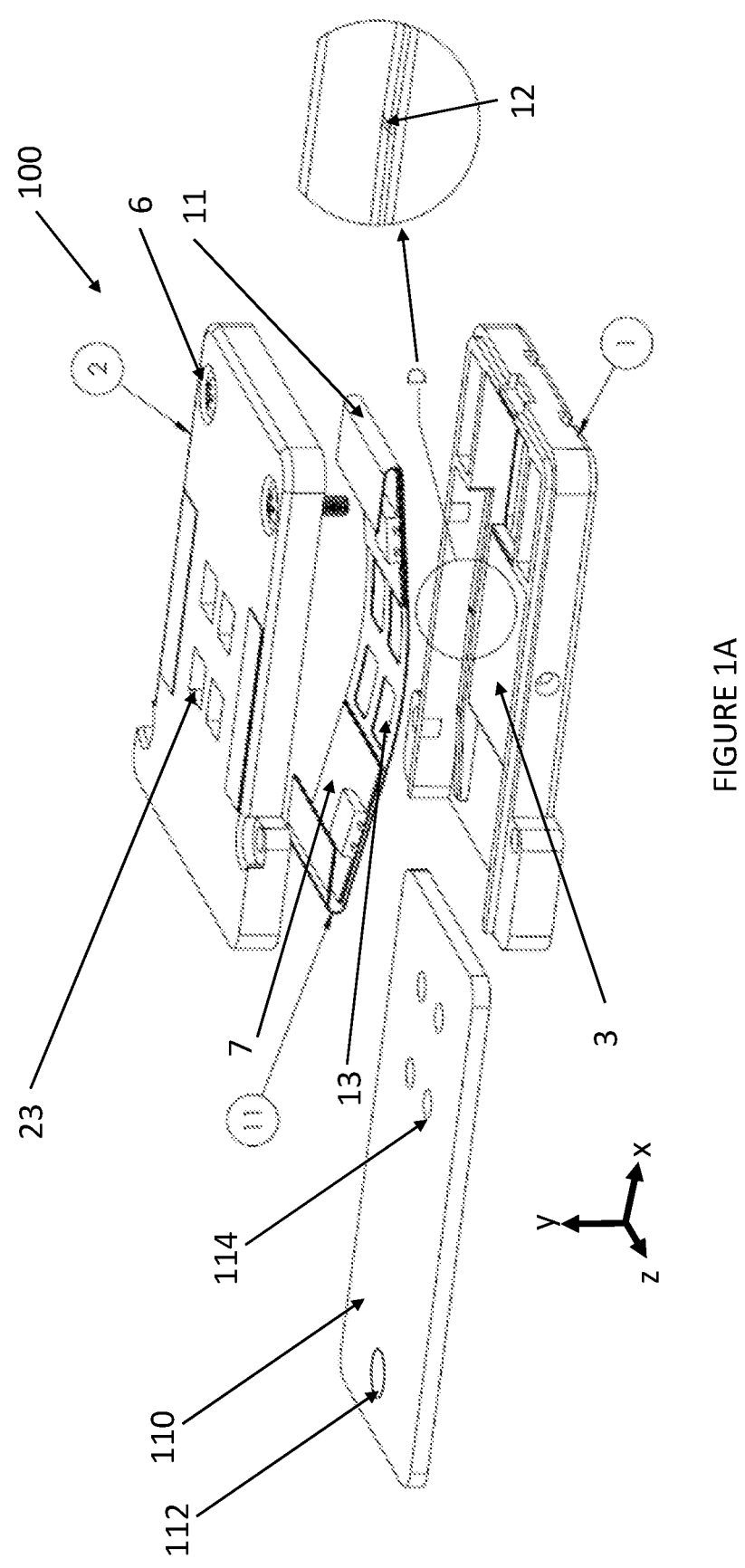
FIG. 1A is an exploded view of a spring heater according to an aspect of the disclosure herein with an inset D showing an enlarged view of a detail.

The following discussion is presented to enable a person skilled in the art to make and use embodiments of the invention. Various modifications to the illustrated embodiments will be readily apparent to those skilled in the art after having studied the teachings in this disclosure, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans, after having studied the teachings in this disclosure, will recognize the examples provided herein have many useful alternatives and fall within the scope of embodiments of the invention.

Disclosure herein are apparatuses that integrate a heater into a microfluidic device and methods or making and using the same. The heater is integrated with a flexible heating and/or spring element that enables the production of an apparatus (which may also be referred to as a device) having a small form factor and light weight. This design allows for the production of devices that are easily portable and handheld. Such devices may be suitable for point-of-care applications.

A point-of-care apparatus and method of using the same for use in clinical and non-clinical settings is described herein. The apparatus is generally useful for nucleic acid amplification testing of a biological fluid ("biofluid") sample, and optional subsequent qualitative or quantitative detection of the presence or absence of a target nucleic acid using a reader. As used herein, the terms "biological fluid" or "biofluid" relate to any fluid produced from a subject including, without limitation, saliva, blood, serum, urine, cerebrospinal fluid, interstitial fluid, cervical fluid, wound fluid, seminal fluid, and other fluid samples.

As used herein, "subject" or "patient" refers to mammals and non-mammals. A "mammal" may be any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats), or laboratory animals including rodents (e.g., rats, mice, and guinea pigs). Examples of non-mammals include, but are not limited to, birds, and the like. The term "subject" does not denote a particular age or sex. In one specific embodiment, a subject is a mammal, preferably a human. The subject may have or suffer from, or be suspected of having or suffering from, a disease, condition, or disorder.

In particular embodiments, the provided apparatus and methods can be used to test a biofluid sample that has been allotted appropriate reaction time to amplify one or more target nucleic acids, including target nucleic acids indicative of potential pathogens, or control nucleic acids within the biofluid sample to generate amplification products. An "amplification product" or "amplicon" is a piece of nucleic acid that is the product of amplification or replication events. The amplification product may also be a source of further amplification or replication events. The "amplification" refers to production of one or more copies of nucleic acid sequence. Amplification of the nucleic acid sequence may be accomplished by various amplification methods known in the art including isothermal and non-isothermal amplification methods.

In some embodiments, the subject may have or suffer from, or be suspected of having or suffering from, an infection by a pathogen. "Pathogen" means an organism that can produce disease in a subject. Examples of pathogens include, without limitation, viruses, bacteria, fungi, and parasites.

The target nucleic acid and the control nucleic acid can, but need not, originate from the same source. For example, the target nucleic acid may originate from a pathogen and the control nucleic acid may originate from the subject. In other embodiments, the both the target and control nucleic acids may originate from the subject. In yet other embodiments, both the target and control nucleic acids may originate from a pathogen.

Some nucleic acid amplification processes can take more than 30 minutes or an hour for target nucleic acids in a biofluid to be properly amplified into a detection sample. In some cases, it may be useful for a user to start the amplification process prior to arriving at a sample reader that reads the detection sample.

Suitably, the amplification technique is an isothermal amplification technique that may additionally comprise reverse transcription (RT) for detection of RNA species. In some cases, the isothermal amplification technique is loop-mediated isothermal amplification (LAMP). Other isothermal amplification techniques may alternatively be used, and include, without limitation, strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), polymerase spiral reaction (PSR), and reverse transcription polymerase chain reaction (RT-PCR). In some cases, reagents for isothermal amplification will vary based on the isothermal amplification technique employed and generally comprise primers and a strand-displacing DNA polymerase, a reverse transcriptase (for detection of RNA species), and/or a DNA helicase. In some cases, the reagents further comprise synthetic nucleic acids (e.g., riboregulators) configured to detect natural nucleic acids from one or more pathogens such as viruses, bacteria, fungi, and parasites.

In some embodiments, the apparatus and methods described herein are capable of analyzing samples at the point of care rather than in a laboratory. As used herein, the term "point of care" or "point of need," which are used interchangeably, can be defined to mean a location on or near a site of patient care where medical or medically related services such as medical testing and/or treatment are provided, including but not limited to hospitals, emergency departments, intensive care units, primary care setting, medical centers, patient homes, physician offices, pharmacies, or sites of an emergency. In some embodiments, "point of care" or "point of need" can be defined as an entry point to a variety of workplaces or gathering locations, such as, for example, airports, train stations, nursing homes, schools, etc. Allowing for the testing of samples collected at or brought to the entry point aids in restricting access to the workplace or gathering location for those who test positive. Further, in some embodiments, the systems and devices of this disclosure are capable of analyzing samples at home to provide regular checks of individuals in a multi-family environment, such as assisted living facilities, dormitories, etc.

FIGS. 1-5 illustrate exemplary embodiments of the invention comprising thermal structures for nucleic acid amplification. Bioassays often require temperatures greater than room temperature to amplify nucleic acids. The presently disclosed technology integrates a heater into a microfluidic device utilizing resistive flexible heating and/or spring elements.

Figure 1B:
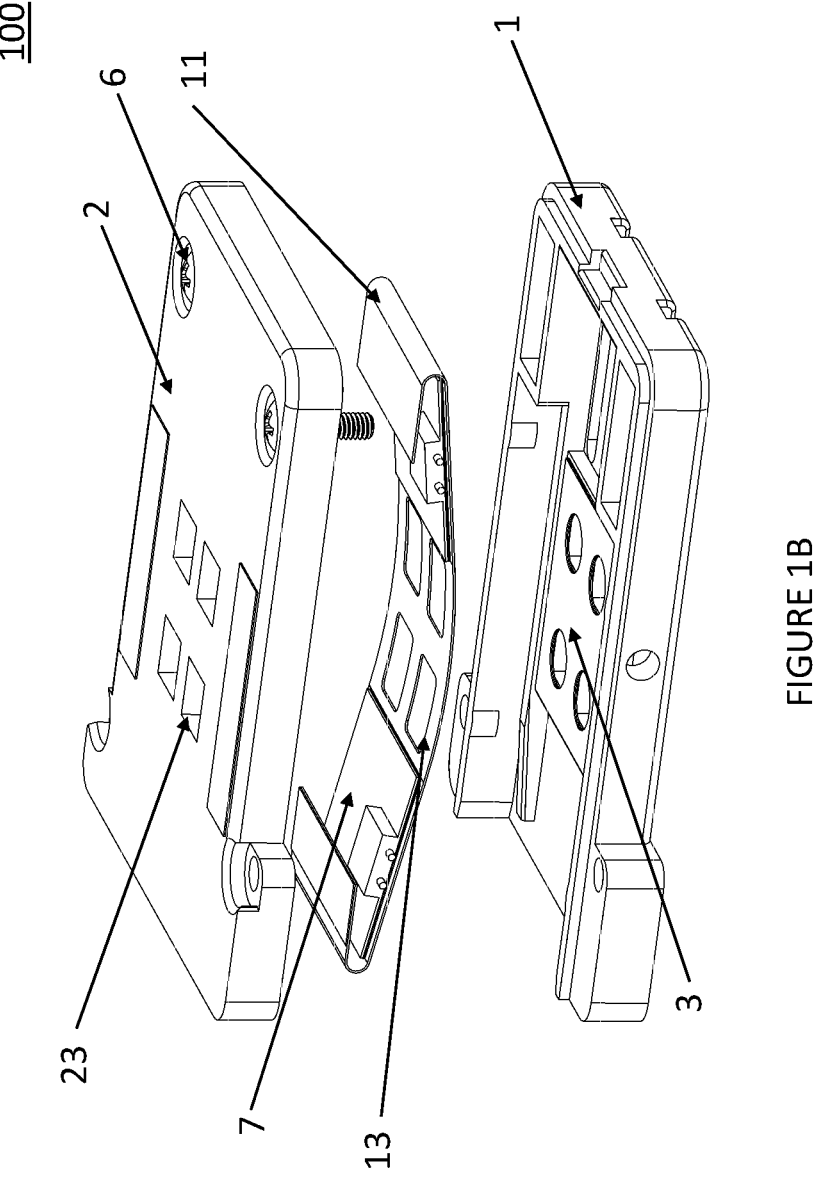
FIG. 1B. is an exploded view of another spring heater according to an aspect of the disclosure herein.

A spring heater 100 comprises a novel implementation of thermal structures in a nucleic acid amplification based bioassay. The spring heater 100 is shown in exploded view in FIG. 1. In the embodiment shown in FIG. 1A, a lower guide 1 and an upper guide 2 comprise an outer casing for the spring heater 100. The spring heater 100 includes an optical filter 3. The optical filter 3 can be attached to a central inner portion of the lower guide 1 as shown in FIG. 1A and can have windows as shown in FIG. 1B. A set of fasteners 6 can hold the lower guide 1 and upper guide 2 together. The spring heater 100 may also comprise side rails of the lower guide 1 having pivot points 12 fore and aft (collinear in z-axis) in FIG. 1A, with a pivot point 12 shown in the enlargement of Detail D. The pivot point 12 may also be used to align or position an inserted microfluidic cartridge or as a detent to prevent motion in an inserted microfluidic cartridge.

As shown in FIG. 1, the spring heater 100 includes a flexible heater 7 and a flexible spring 11. The flexible heater 7 can be planar with two opposing sides. The flexible spring 11 can be, for example, a leaf spring. The flexible spring 11 can be a strip having a curved central portion between two linear portions, where both ends of the strip are bent back over towards the concave side of the strip. The flexible heater 7 can be located at the linear portion of the flexible spring 11.

Figure 2:
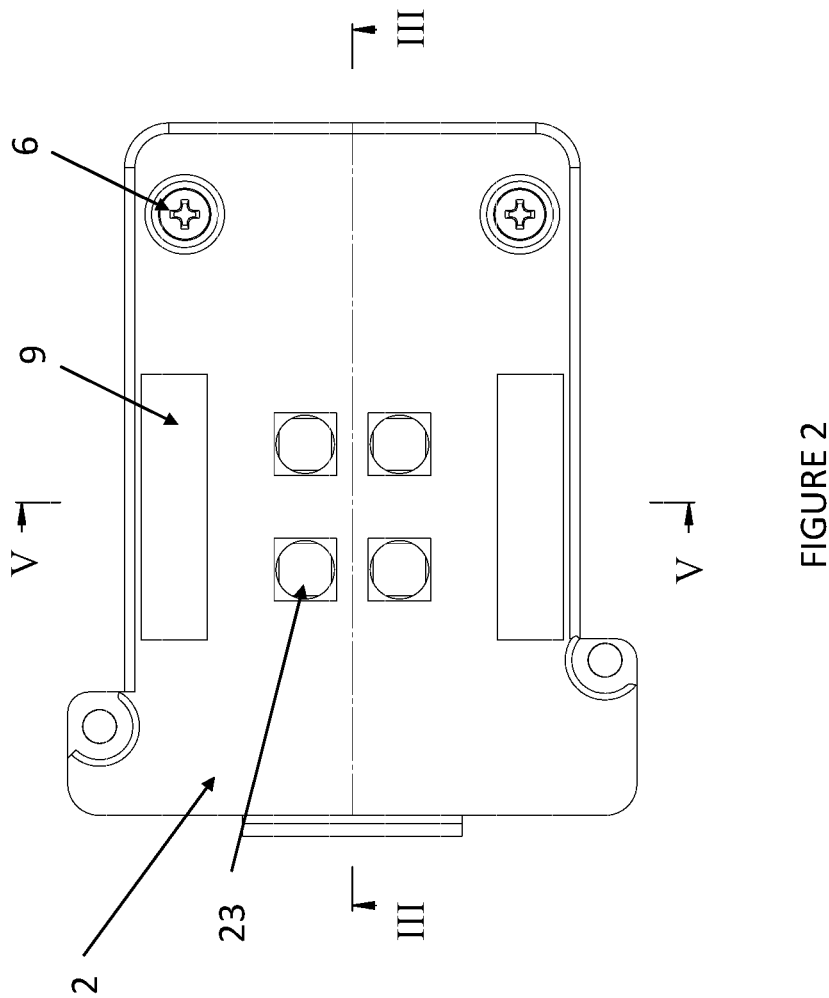
FIG. 2 is a top view of the spring heater of FIG. 1A.

The spring 11 can include a group of spaced apertures 13 in the central curved region. The apertures 13 can be rectangular as shown in FIG. 1, however other shapes and spacings are contemplated. FIGS. 1-2 show the upper guide 2 which can include a set of windows 23 arranged generally in the central region of the upper guide 2. When assembled, the apertures 13 align with the windows 23. The spring heater 100 can include a tape shim 9 on the top of upper guide 2.

In some embodiments, the spring heater 100 can be used with a cartridge 110. The cartridge 110 can include at least one sample opening 112 for entry of a biofluid sample. The sample opening 112 is in fluid communication with at least one microfluidic channel (not shown) within the cartridge 110. In some embodiments, the spring heater 100 is configured to apply heat to the cartridge 110 adjacent with at least one of the microfluidic channels (not shown) within the cartridge 110. The cartridge 110 further includes wells 114 that allow for detection of a substance of interest, e.g., a dye, within the cartridge 110 by a detector outside of the cartridge 110 or by visual inspection. The wells 114 are sealed fluidically via a cover layer (not shown) so that the fluid cannot contact the heater, upper and lower guides, and other features shown in FIG. 1 with the exception of the channels (not shown) and inlet 112 in the cartridge 110. When the cartridge 110 is inserted into the spring heater 100, the wells 114 align with apertures 13 and windows 23.

Figure 3:
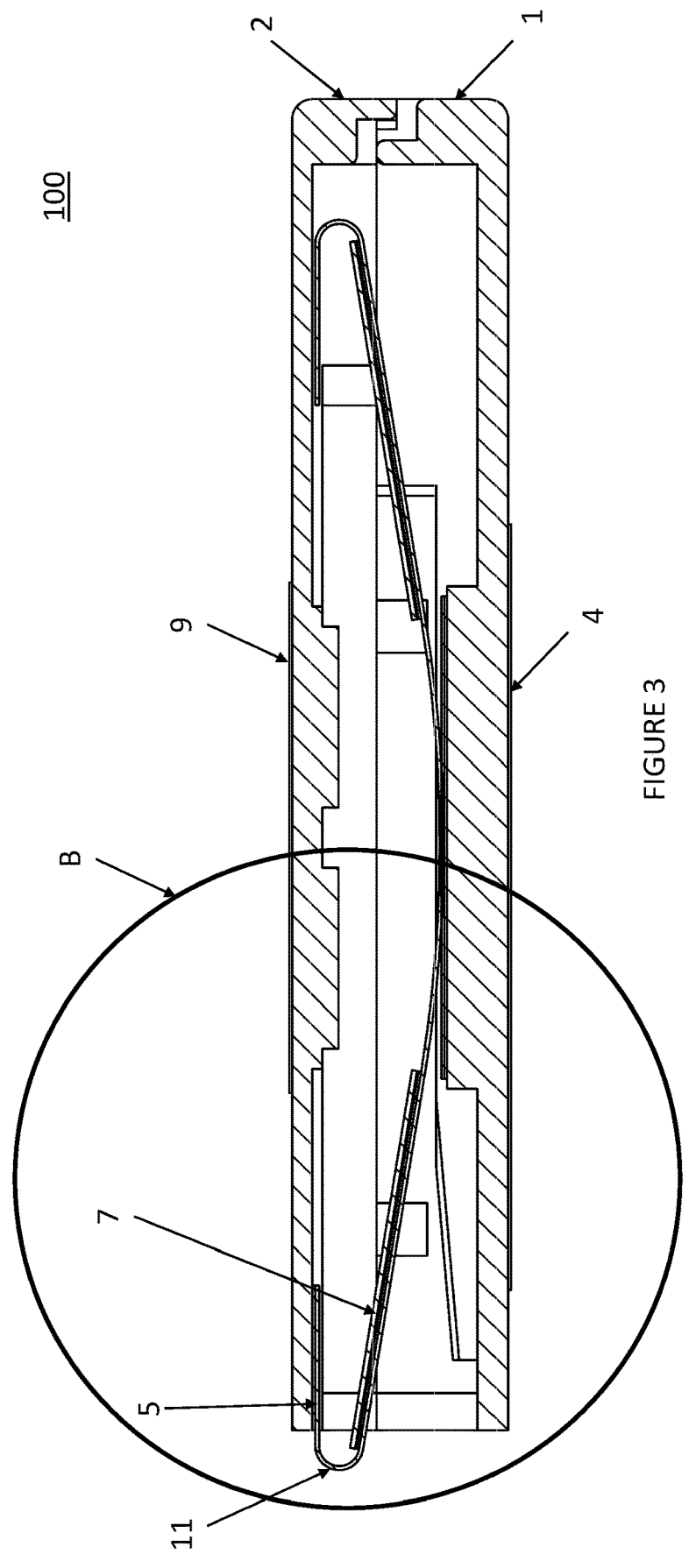
FIG. 3 is a cross-sectional view of the spring heater of FIG. 1A.
Figure 4:
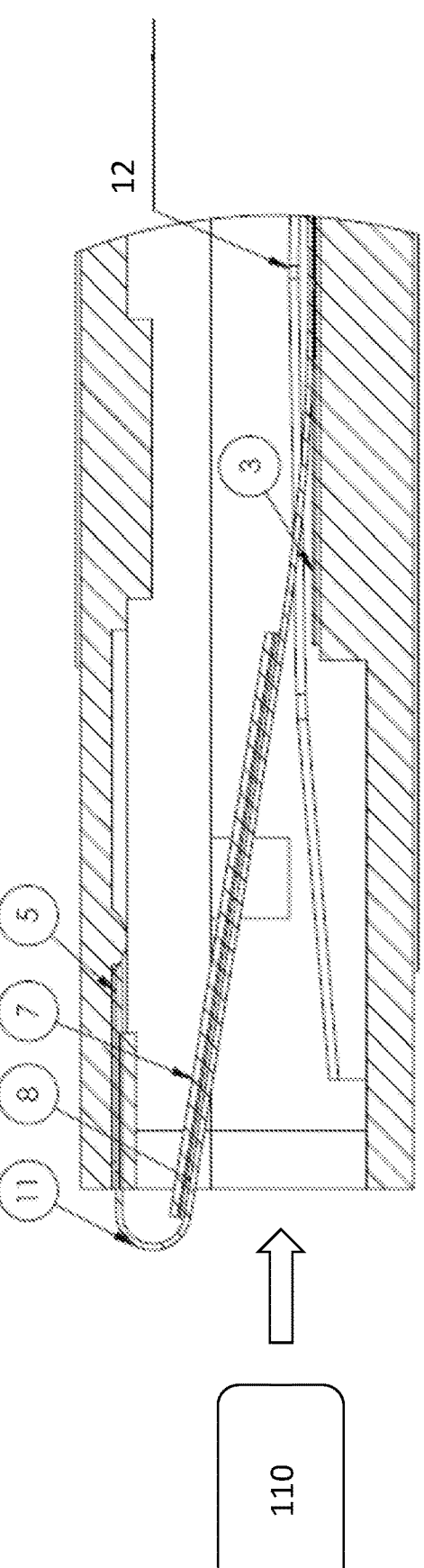
FIG. 4 is another cross-sectional view of the spring heater of FIG. 1A.
Figure 5:
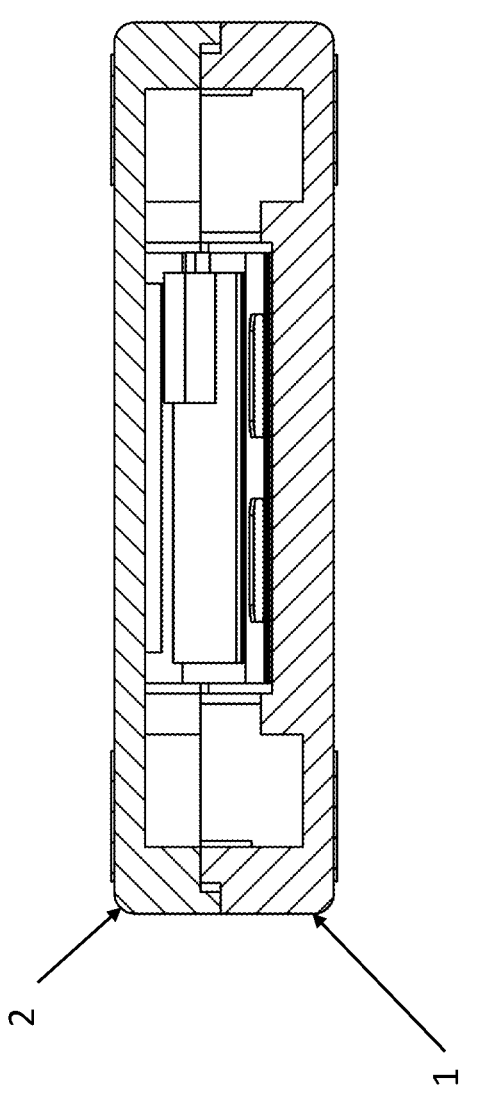
FIG. 5 is an enlarged view of a portion of the cross-sectional view of FIG. 4.
Figure 6:
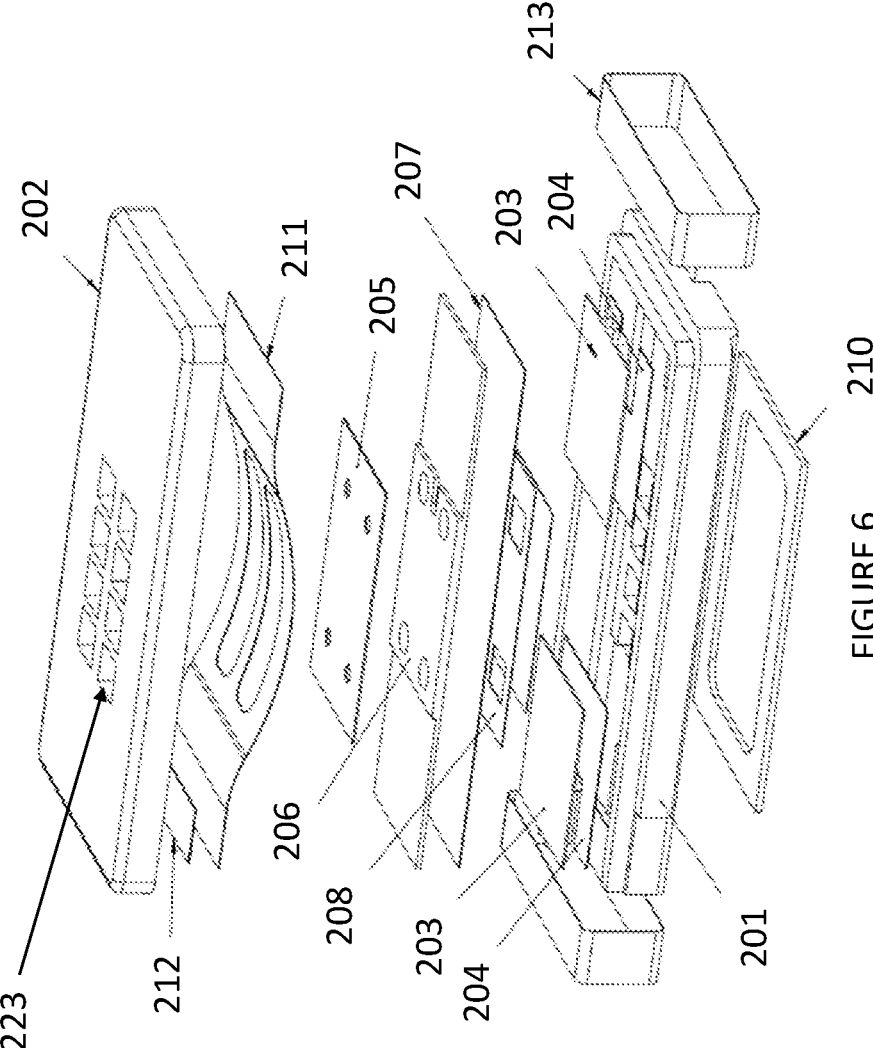
FIG. 6 is an exploded view of another spring heater, according to an aspect of the disclosure.

The cross-sectional view in FIGS. 3-4 shows the spring heater 100 further includes a board attachment adhesive 4 on the bottom of lower guide 1. The flexible heater 7 and flexible spring 11 are encased by the lower guide 1 and upper guide 2. More specifically as shown in detail in FIG. 4 (enlargement of region B in FIG. 3), the flexible heater 7 is affixed to the flexible spring 11 by an attachment 8 on the concave side of the flexible spring 11. The attachment 8 connects a surface of the flexible heater 7 to the concave side of the flexible spring 11, and can be, for example, a pressure-sensitive adhesive (PSA) while other types of chemical or physical bonding are also contemplated. A substantial portion of the surface of one side of the flexible heater 7 is in contact with the surface of the flexible spring 11. The surface contact between the flexible heater 7 and flexible spring 11 enables effective heat transfer from the heater 7 through the spring 11 to a microfluidic cartridge 110. The spring 11 may be made of metal alloy, such as beryllium-copper alloy C17200, phosphor-bronze, plated spring-steel, or other suitable material having sufficient yield strength and thermal conductivity.

In operation, the cartridge 110 is inserted into one end of the spring heater 100 where it first abuts the spring 11 and slides along the side rails of the lower guide 1. As the cartridge is pushed into the spring heater 100, the cartridge 100 pressed against spring 11, which is thereby deflected and flattens.

Once the cartridge 100 is fully inserted, the spring 11 confronts a portion of the surface of the cartridge 110. More specifically, the region of the spring 11 having the heater 7 on the opposing side contacts a portion of the cartridge 110. This arrangement allows heat to transfer through the spring 11 to the cartridge 110. The curvature of the flexible spring 11 in the region of contact with the cartridge 110 may be such that upon deflection, the region of contact of the spring becomes effectively flat to enable good heat transfer to the cartridge 110.

The spring heater 100 enables mounting of the spring 11 to the thermally-insulating upper guide 2 at one end (FIGS. 3-4). More specifically, one bent end of the spring 11 is fixed to the upper guide 2 at a guide attach 5. The opposite end is constrained laterally (z-axis in FIG. 1) and is simply supported vertically (y-axis) but is allowed to float longitudinally (x-axis) thus greatly reducing the spring rate versus being constrained at both ends. In other words, the spring 11 has the flexibility to flatten when the cartridge 110 is inserted because it is fixed to upper guide 2 at one bent end, but not at the opposing end.

The spring 11 has torsional compliance especially in the region of contact due to the apertures in the spring 11 and due to the high aspect ratio of the contact region length (e.g., x=30 mm) and width (e.g., z=22 mm) relative to the sheet metal thickness (y), which may be about 0.15 to 0.2 mm. Torsional compliance is beneficial to enable good thermal contact in spite of manufacturing tolerances in warp, bow and twist of the cartridge 110 and spring 11, and error in parallelism between the cartridge 110 and contact surface of the spring 11.

The pivot point 12 in the side rails of lower guide 1 serves to minimize the contact area and maximize contact resistance between the cartridge 110 and the lower guide 1 in order to minimize heat loss. The cartridge 110 does not make contact with optical filter 3, thus enabling good thermal resistance with low heat loss. When the cartridge 110 is inserted, force is applied between the spring 11 and the cartridge 110 such that thermal contact resistance is minimized between the spring 11 and the cartridge 110, and such that thermal contact resistance is maximized between the spring 11 and the lower and upper guides 1, 2. The configuration of the spring 11 and the lower and upper guides 1, 2 is such that the heater 7 can be somewhat thermally isolated from the lower and upper guides 1, 2 when the cartridge 110 is inserted and the spring is in the flattened or deflected state, or when the cartridge 110 is not inserted and the spring 11 is in an undeflected or less deflected state.

The apertures 13 can also serve to allow passage of light for optical analysis of the bioassay. For example, the spring apertures 13 can allow optical transmission of emitted fluorescence through the spring apertures 13 and windows 23 to the detectors (not shown) positioned above the upper guide 2. In another embodiment, the apertures 13 may be circular, or nearly circular, with an exemplary diameter of about 3 mm each, in order to reduce unwanted light (escaped excitation) from reaching the detectors. The flexible spring 11 may be assembled with the apertures 13 offset left of center (x-axis) in the undeflected state so that when the cartridge 110 is inserted, the spring 11 is in the deflected state and the apertures 13 are on center.

In another embodiment shown in FIGS. 6-10, a spring heater 200 includes a lower guide 201, an upper guide 202, and a set of heaters 203. As shown in the exploded view of FIG. 6, the heaters 203 are fixed on one side to the lower guide 201 by a heater adhesive 204. On the other side, opposite to the lower guide 201, the heaters 203 are mounted to a heat spreader 206 using a heat spreader adhesive 207. The heat spreader 206 has a high thermal conductivity that moves heat away from the heaters 203. The heat spreader 206 is at least partially covered on a top side by a heat spreader mask 205 that helps thermally isolate the heaters 203 and heat spreader 206.

The spring heater 200 can include a guide spring 211. The guide spring 211 is a strip with a curved central region. The ends of the guide spring 211 are flat. The guide spring 211 is fixed at one end to the upper guide 202 by a guide attach 212. The upper guide 202 can include a group of windows 223.

Figure 7:
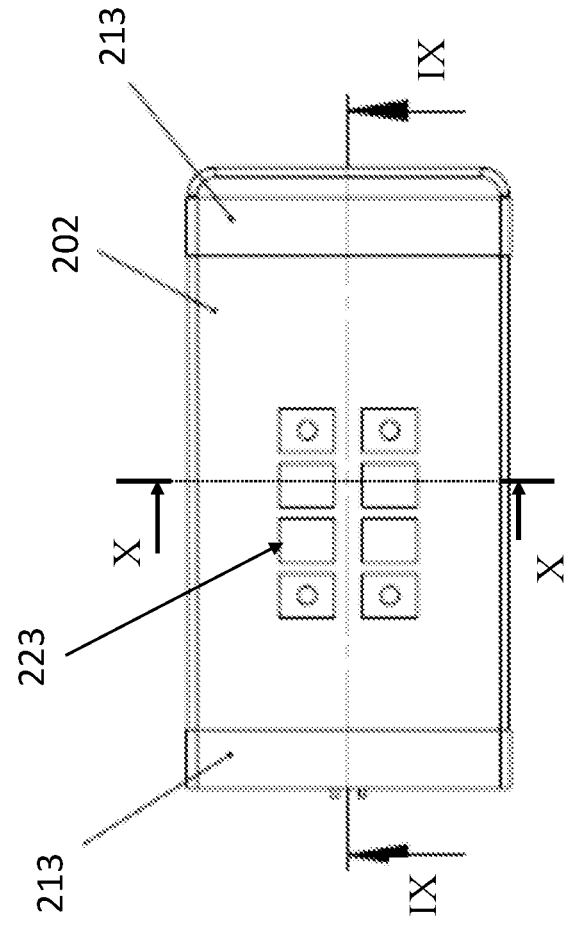
FIG. 7 is a top view of the spring heater of FIG. 6.

The top view of the spring heater 200 in FIG. 7 shows at least one band 213 that can be used to hold the lower and upper guides 201, 202 together. The windows can be arranged in a 4×2 array as shown, however other array and spacing configurations are contemplated.

Figure 8:
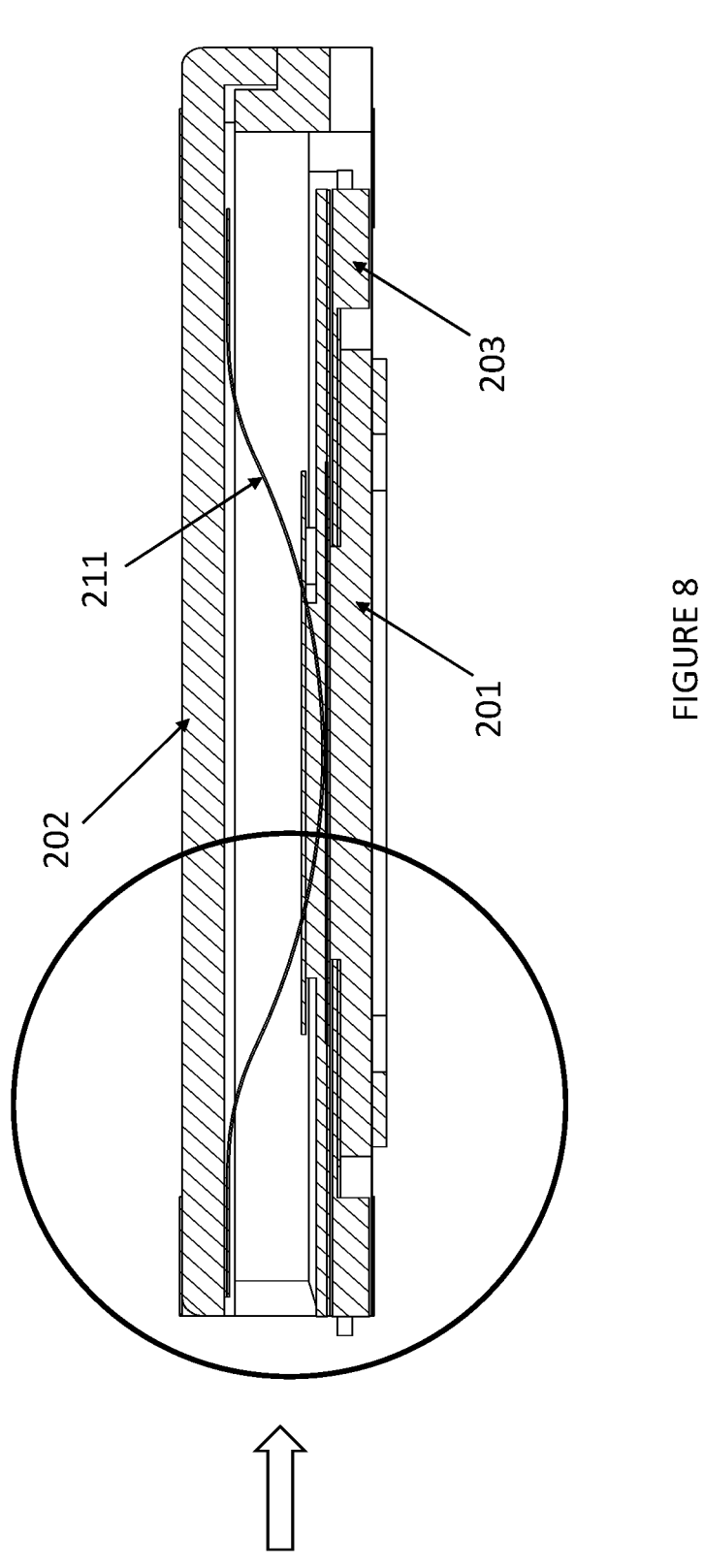
FIG. 8 is a cross-sectional view of the spring heater of FIG. 6.
Figure 9:
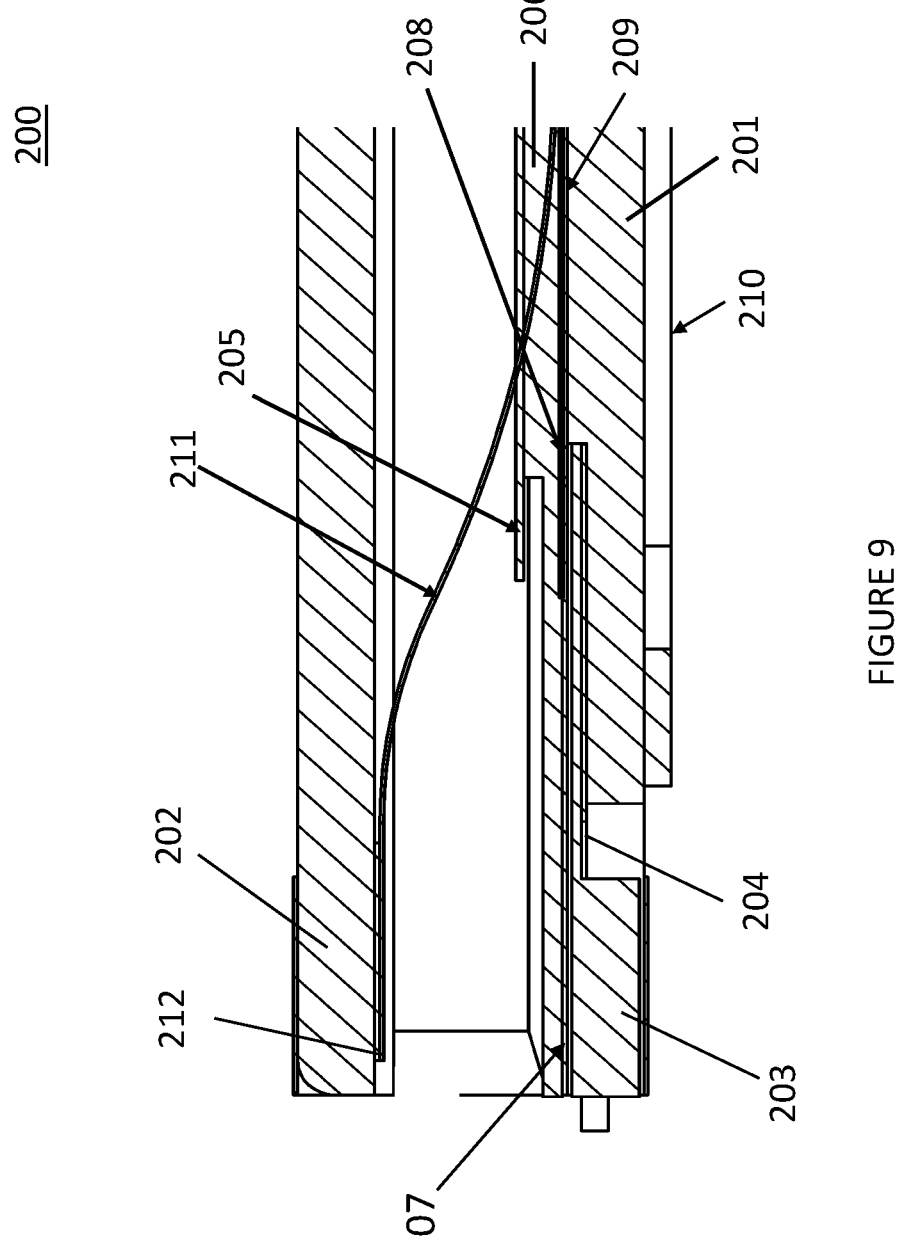
FIG. 9 is an enlarged view of a portion of the cross-sectional view of FIG. 8.
Figure 10:
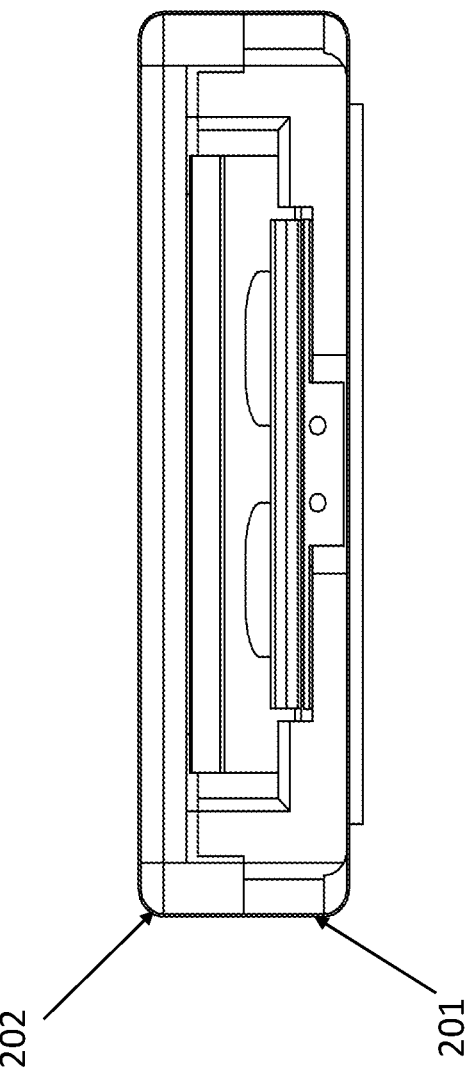
FIG. 10 is another cross-sectional view of the spring heater of FIG. 6.

FIGS. 8-9 shows a cross sectional view of the spring heater 200. The guide spring is attached to the upper guide 202. The heat spreader 206 is attached to the lower guide 201. Additional details from the circled region in FIG. 8 can be seen in FIG. 9. In this configuration, heat from the heaters 203 moves to the heat spreader 206 and then to the cartridge 110. The heaters 203 and heat spreader 206 preferably have minimal contact area with the lower guide 201; thus, heat loss to the lower guide 201 is minimized. The spring heater 200 can include a mask for optical filters 208, a optical filter 209, and a board shim 210.

In operation, the cartridge 110 enters the spring heater 200 through an open end as indicated by the open arrow. Upon entry of the cartridge 110 the curved central region of the guide spring 211 is pressed upwards such that it deflects and flattens, while anchored to the upper guide 202 at one end. Once the cartridge is fully inserted, the spring 211 is located above the cartridge 110 (not shown) and the spring force helps hold the cartridge 110 in place against the heat spreader 206, mounted below the cartridge 110. The heat spreader 206 is designed to minimize contact with the lower guide 201 to minimize heat loss. The purpose of the spring 211 is to ensure good thermal contact between the cartridge 110 and the heat spreader 206. In this embodiment, the guide spring 211 may be made of stainless steel, which has lower thermal conductivity and higher elastic modulus (allowing a thinner spring) compared with copper-based alloys, to minimize heat transfer to and through the spring. Additionally and alternatively, the guide spring 211 can be made of a polymeric material.

The cartridge 110 may host an isothermal amplification technique that may comprise reverse transcription (RT) for detection of RNA species. In some cases, the isothermal amplification technique is loop-mediated isothermal amplification (LAMP). The spring heater 100 has been tested with Loop-mediated amplification (LAMP). LAMP is a type of nucleic acid amplification test (NAAT) that requires elevated temperature, but not rapid cooling as does traditional polymerase chain reaction (PCR). Effective heat transfer is needed between a heater and the microfluidic device, minimizing temperature drop and latency in transient response. It can be used with other reactions that require thermal control such as PCR or other techniques. The heater can provide one or more heating periods spaced by cooling periods. The time to reach the required heating temperature can be varied.

In some embodiments, the cartridge 110 and spring heater 100 can be used with a reader (not shown) that is configured to accept (or receive) the cartridge 110 and produce a qualitative or quantitative output. The reader can includes a detection inlet 162 that receives the cartridge 110. The reader may provide electromagnetic radiation that may be absorbed by the biofluid sample within the cartridge 110. The electromagnetic radiation may be of any suitable wavelength that can provide a detectable signal indicating the presence or absence of an amplification product of a target nucleic acid. In some embodiments, the electromagnetic radiation may be of any suitable wavelength that can provide a detectable signal indicating the presence or absence of an amplification product of a control nucleic acid. In some embodiments, the excitation array provides electromagnetic radiation in the infrared, visible, or ultraviolet spectrums. The reader may emit broadband or narrowband electromagnetic spectrums.

The reader may include a photodetector that detects any suitable wavelength of electromagnetic radiation. In some embodiments, the photodetector detects electromagnetic radiation in the infrared, visible, or ultraviolet spectrums. The photodetector may include an array connected to a readout circuit, which can include a microchip. The photodetector can wirelessly communicate or communicate through a wired connection to a processor (not shown) that can decode and translate intensities sent via a digital signal that originate from a current signal. The detection sample may include biomarkers, chromophores, fluorophores, dyes, and other compounds or substances capable of emitting light of a second wavelength or color when stimulated by a first light of a first wavelength or color. The presence of amplification products of the target and/or control nucleic acid sequence in the second biofluid sample may alter electromagnetic radiation intensity emitted at the second wavelength relative to an amplification product free second biofluid sample. The photodetector can detect the light of the second color and output the current which is then transmitted to the processor. The intensity of the detected light allows for determination of the presence or absence of the target nucleic acid and/or control nucleic acid target. The processor can output qualitative or quantitative results that can be used for epidemiological data collection and studies.

In some embodiments, the reader can further include an indicator (not shown). The indicator can include one or more of an audio, visual, or tactile indication. For example, the indicator may output a light (e.g., a green light or a red light) if a specific pathogen at a predetermined level is found (or not found) in the detection sample.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An apparatus comprising a flexible heater in thermal contact with a flexible spring, wherein the flexible spring is configured to provide thermal energy from the heater to a microfluidic cartridge received by the apparatus when the microfluidic cartridge is in contact with the flexible spring, wherein the flexible heater is affixed to the flexible spring, and wherein the flexible spring comprises apertures offset from center in an undeflected state and configured to center in a deflected state when contacted with the microfluidic cartridge.

2. The apparatus of claim 1, wherein the flexible spring comprises a metal alloy.

3. The apparatus of claim 1, wherein the flexible spring flattens when contacted with the microfluidic cartridge.

4. The apparatus of claim 1, wherein the flexible spring is a leaf spring.

5. A system for amplification of a target nucleic acid comprising the apparatus according to claim 1 and a cartridge dimensioned to be received by the apparatus and contact the flexible spring when received by the apparatus, wherein the microfluidic cartridge has reagents for performing an amplification reaction therein.

6. A method comprising heating a microfluidic cartridge in contact with the flexible spring of the apparatus of claim 1, wherein the microfluidic cartridge comprises a biofluid sample therein and wherein heating the microfluidic cartridge with the apparatus provides sufficient thermal energy to perform an amplification reaction to generate amplification products of a target nucleic acid.

7. The method of claim 6, wherein the microfluidic cartridge has reagents for isothermal amplification therein.

8. The method of claim 7, wherein the microfluidic cartridge has reagents for LAMP or RT-LAMP therein.

9. The method of claim 6 further comprising detecting for amplification products.

\* \* \* \* \*